(12) United States Patent
Henninger et al.

(10) Patent No.: US 10,426,702 B2
(45) Date of Patent: Oct. 1, 2019

(54) MIXING AND/OR TRANSFERRING DEVICE

(71) Applicant: sfm medical devices GmbH, Wächtersbach (DE)

(72) Inventors: Peter Henninger, Brachttal (DE); Markus Kehr, Biebergemünd (DE)

(73) Assignee: SFM MEDICAL DEVICES GMBH, Wächtersbach (DE)

( * ) Notice: Subject to any disclaimer, the term of this patent is extended or adjusted under 35 U.S.C. 154(b) by 51 days.

(21) Appl. No.: 15/306,933

(22) PCT Filed: Dec. 23, 2015

(86) PCT No.: PCT/EP2015/081196
§ 371 (c)(1),
(2) Date: Oct. 26, 2016

(87) PCT Pub. No.: WO2016/107811
PCT Pub. Date: Jul. 7, 2016

(65) Prior Publication Data
US 2017/0290742 A1 Oct. 12, 2017

(30) Foreign Application Priority Data

Dec. 30, 2014 (DE) .................. 10 2014 119 712
May 11, 2015 (DE) .................. 10 2015 107 312

(51) Int. Cl.
*A61J 1/20* (2006.01)
*B65D 81/32* (2006.01)

(52) U.S. Cl.
CPC ........... *A61J 1/2065* (2015.05); *A61J 1/2089* (2013.01); *A61J 1/2055* (2015.05); *A61M 2207/00* (2013.01); *B65D 81/3211* (2013.01)

(58) Field of Classification Search
CPC ............................................. A61F 1/20–2096
See application file for complete search history.

(56) References Cited

U.S. PATENT DOCUMENTS 5,350,372 A 9/1994 Ikeda et al.
5,879,345 A 3/1999 Aneas
(Continued)

FOREIGN PATENT DOCUMENTS

DE 693 20 400 T2 12/1998
DE 100 30 474 C1 2/2002
(Continued)

OTHER PUBLICATIONS

International Search Report dated Apr. 5, 2016 for Application No. PCT/EP2015/081196.
(Continued)

*Primary Examiner* — Benjamin J Klein
(74) *Attorney, Agent, or Firm* — Ladas & Parry LLP; Malcolm J. MacDonald

(57) ABSTRACT

A device for mixing a first substance and a second substance, or for transferring at least one of the substances, which are present in a first or second receptacle, the device including a first adapter with a circumferential wall, along which extends a cannula body, and a hollow-cylindrical section that is connected to the cannula body; a second adapter with a circumferential wall, along which extends a cannula body; and a hollow-cylindrical section that is connected to the cannula body; when the first and the second adapter are assembled, the hollow-cylindrical sections inter-engage in a liquid-tight manner, and the first and the second adapter are connected to each other in a detachably screwed manner.

28 Claims, 10 Drawing Sheets

(56) References Cited

U.S. PATENT DOCUMENTS

Figure 1:
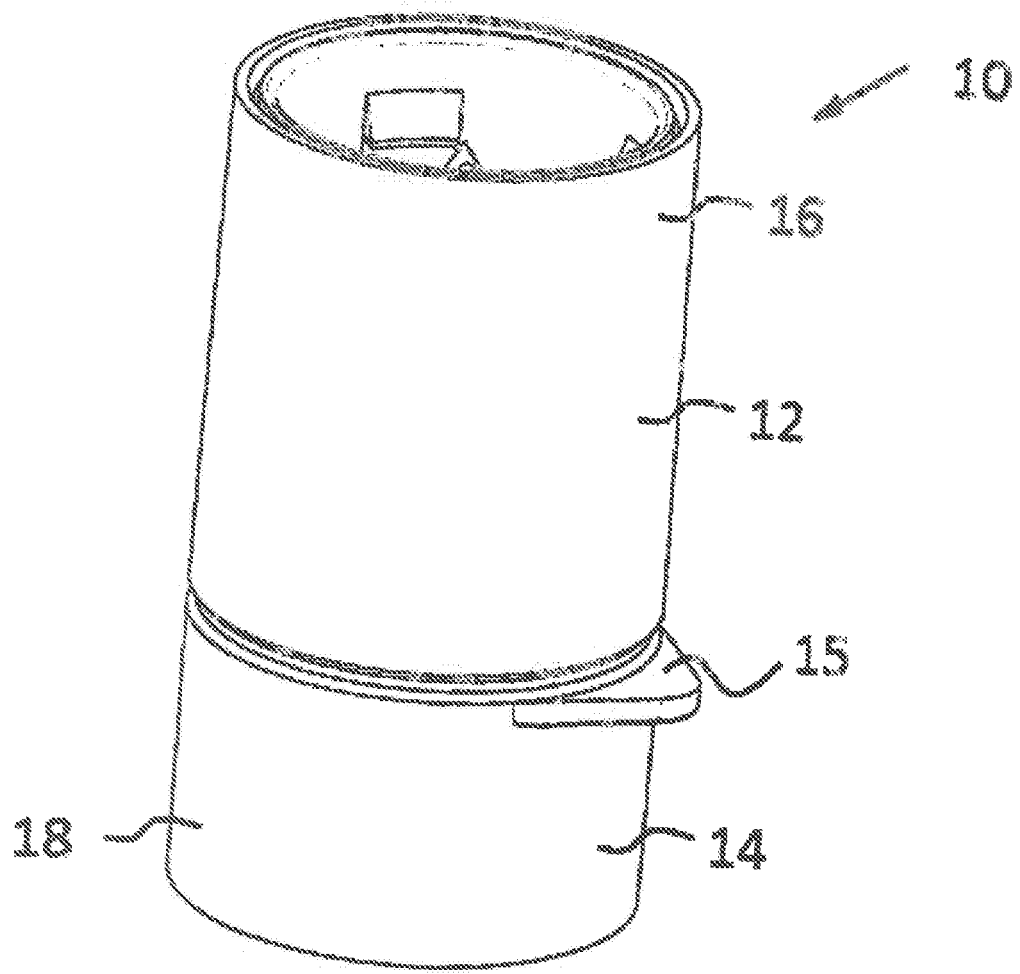

| | | | |
|---|---|---|---|
| 6,558,365 | B2 | 5/2003 | Zinger et al. |
| 6,948,522 | B2 | 9/2005 | Newbrough et al. |
| 8,857,470 | B2 | 10/2014 | Rahimy et al. |
| 2002/0087141 | A1 | 7/2002 | Zinger et al. |
| 2005/0033260 | A1* | 2/2005 | Kubo .................... A61J 1/2089 604/411 |
| 2012/0323210 | A1* | 12/2012 | Lev ....................... A61J 1/2089 604/405 |

FOREIGN PATENT DOCUMENTS

| | | |
|---|---|---|
| DE | 10 2004 005 435 B3 | 9/2005 |
| DE | 10 2006 031 712 B3 | 12/2007 |
| DE | 10 2008 002 800 A1 | 9/2009 |
| EP | 1 498 097 A2 | 1/2005 |
| WO | 92/11897 A1 | 7/1992 |
| WO | 2005/041846 A2 | 5/2005 |
| WO | 2009112489 A1 | 9/2009 |
| WO | WO 2009112489 A1 * | 9/2009 ............ A61J 1/2089 |

OTHER PUBLICATIONS

Espacenet English abstract of WO 2009/112489 A1 which corresponds to DE 10 2008 002 800 A1.
Espacenet English abstract of EP 0 570 939 A1 which corresponds to DE 693 20 400 T2.
Espacenet English abstract of DE 10 2006 031 712 B3.
Espacenet English abstract of WO 2005/074860 A1 which corresponds to DE 10 2004 005 435 B3.
Espacenet English abstract of DE 100 30 474 C1.
South Korean Office Action, dated Mar. 18, 2019, corresponding to Application No. 10-2016-7031852.

\* cited by examiner

MIXING AND/OR TRANSFERRING DEVICE

The invention relates to a mixing and/or transfer device for mixing a first substance and a second substance or for transferring at least one of the substances, which are present in a first or second receptacle, comprising a first adapter with a circumferential wall, which is suitable for accepting the first receptacle, and along which extends, and which at least in sections surrounds, a cannula body, as well as a hollow-cylindrical section that is connected to the cannula body, a second adapter with a circumferential wall, which is suitable for accepting the second receptacle, and along which extends, and which at least in sections surrounds, a cannula body, as well as a hollow-cylindrical section that is connected to the cannula body, whereby when the first and the second adapter have been assembled, the hollow-cylindrical sections preferably inter-engage in a liquid-tight manner and the first and the second adapter are connected to each other in a detachable screwed manner.

In a mixing device in accordance with U.S. Pat. No. 6,558,365, for the purpose of mixing the fluids present in the receptacles, one of which in particular can be a medical substance in powder form with the other one being a liquid, the adapters are initially connected to each other in the manner of a screwed connection via Luer Lock cones. Subsequently, the receptacles, which are sealed by pierce-able caps, are introduced into the accommodations that are formed by circumferential walls. Since the receptacle, which is partially filled with powder, is at negative pressure, the liquid contained in the other receptacle is drawn in, so that subsequently the mixing of the liquid with the medical agent can proceed. Now the adapters are separated from each other, in order to connect the adapter that contains the medical agent to a syringe, for example. A Luer Lock cone is used to create a connection to a syringe in a simple manner.

In this regard the design has the disadvantage that the connection between the adapters is accomplished by means of the Luer Lock cones situated in the centre, so forces acting upon circumferential walls, which possess a significantly greater diameter, can result in an unintentional disconnection. When the adapters have been attached to each other, the bottom walls are separated from each other by a distance, so that the adapters can be moved relative to each other, which can bend the link across the hollow-cylindrical sections. Also, during the screwing-together of the adapters, one faces the risks of jamming due to a tilted orientation or a break in the Luer region.

DE-B-10 2006 031 712 discloses a medical transfer device that consists of a tubular part to accept a first bottle and—axially movable relative to the latter part—a holder component for accepting a second bottle. A flange is arranged axially moveable in the holder component. To create a connection between the bottles it is necessary for the bottle that is accepted by the tubular component to be axially moved inside the latter, in order to spread brackets originating from the component in such a way that the holder component can be moved together with the flange inside the tubular part/component.

A medical transfer device in accordance with DE-B-10 2004 005 435 is embodied in three parts, whereby in this case it is also necessary to axially shift the components relative to each other in order to create a connection between the bottles accommodated by the outer components.

A connector for medical liquids in accordance with DE-C-100 30 474 comprises a connecting element that consists of sections that have been joined by ultrasonic welding.

Known from EP-A-1 498 097 is a transfer device that comprises two adapters. For the purpose of connecting the adapters, a groove is present in the circumferential wall of one adapter, into which engages a projection originating from the circumferential wall of the other adapter.

In the transfer system according to WO-A-92/11897, the adapters of a transfer system are joined by screwing them together.

Subject matter of WO-A-2005/041846 is a transfer system, in which an adapter with a vial is connected to another adapter with a flexible receptacle. The adapters are connected to each other via a connecting element.

In a mixing device in accordance with DE-B-10 2008 002 800 A1, elements serving to connect adapter components may originate from the latter and form-fittingly interlock.

The objective of the present inventions is to further develop a transfer or mixing device of the above-mentioned type in such a manner that it will be easy to operate but still offers sufficient stability, in particular to rule out that handling the adapter components from the outside can inadvertently result in a change of position of the receptacles—also known as vials—to be accepted by the components. Also, if required, the option should be available to be able to use simple measures to adapt to receptacles of different sizes.

A further aspect of the invention is intended to create the option that after the medication has been prepared, it can be withdrawn from the vial into a syringe without an additional cannula.

Also provided should be the option of filtering a prepared medicinal product, such as lyophilisate. If necessary, this should also be the case for the liquid, such as water.

The option of a needle-free operation should be provided as well.

Moreover, the device should remain closed until such time when the medication is being withdrawn.

A simple operability should be offered, so that persons with limited motor skills can also operate the device.

To meet this objective or aspects thereof it is fundamentally intended that both the first and the second adapter comprise a hollow-cylindrical outer body with an exterior circumferential wall as well as a partition wall that extends perpendicular to the longitudinal axis of the outer body, that when the adapters have been assembled, a section equipped with an internal thread of the outer circumferential wall of the one adapter surrounds a section equipped with an external thread of the circumferential wall of the other adapter, whereby the threaded sections inter-engage, and that the hollow-cylindrical outer body of the first and/or the second adapter comprise an insert with a circumferential wall that accommodates the first or the second receptacle.

The term hollow-cylindrical is to be understood to mean that a hollow-cylinder geometry should be present in principle even though the outer body may possess on its outside a geometry that differs from this. In particular, the term hollow-cylindrical exterior body also encompasses a body with an exterior geometry that resembles that of a multi-sided column, such as a cuboid shape. In this respect the term hollow-cylindrical should be treated as a synonym. However, the term hollow-cylindrical exterior body is meant to convey that the exterior body possesses a cylindrical geometry on its inside.

In particular it is intended that each adapter comprises an insert with a circumferential wall that accepts the first or the second receptacle.

Diverging from category-defining designs known in the art, in which the adapters are screwed together to connect them, a separate element is provided to accept the receptacle which is situated within the hollow-cylindrical or hollow-body-shaped outer body, which also can be referred to as a housing, so that the latter may consist of a comparatively rigid material, in particular plastic, and can maintain its geometry during any handling of the outer body. In contrast, prior art adapters for accepting vials would possess sections along their circumference that are separated by slots, resulting in some flexibility of the adapter components along the circumference.

The fact that an insert is provided to accept the vial results in a modular structure with the benefit that without any modification of the geometry of the outer component, i.e. of the hollow-cylindrical outer body, inserts of various cross-sectional profiles can be introduced to be matched to vials of various dimensions, in order to fix these in position to the required degree.

The hollow-cylindrical or hollow-body-shaped exterior bodies of the adapters form a housing that at least in sections can possess a cylindrical and/or cuboid geometry. In particular the adapter that accepts a vial with a medical substance possesses a cylindrical exterior geometry. The other adapter may possess a cuboid exterior geometry. Independently thereof there is no absolute need for a flush transition between the outer surfaces, even though this is possible in at least some sections.

Once the adapter components have been assembled, i.e. have been screwed together, a gap or slot or circumferential recess may be present between them. Irrespective thereof, the adapter components possess the required stability and a tilting and jamming of the adapter components is ruled out, since the latter inter-engage in sections. In addition, a front surface of one adapter may extend along a step of the other adapter or may be aligned with the step at a distance, so that in principle a tilted assembly is ruled out.

Because of the modular structure, i.e. because of the insert, which can be inserted into the outer hollow-cylinder or hollow-cylindrical body, and which in particular is connected in a material bond with the latter, one benefits from the additional advantage that it is easy to position and fix in position a filter element between the bottom wall of the insert and the partition wall of the hollow-cylindrical or hollow-bodied exterior body. This element can be connected, e.g. welded, beforehand to the outer surface of the bottom wall of the insert, in order to subsequently connect, in particular in a material bond by means of ultrasonic welding, the insert and the partition wall of the hollow-cylinder or hollow-cylindrical outer body in such a way that the bottom wall is joined in a liquid-tight manner to the partition wall. This ensures that when the adapters are connected, the liquid flowing through the hollow-cylindrical section that in particular is embodied as a Luer cone or Luer Lock cone if female and as a Luer if male, flows exclusively through the filter from the one vial into the other vial. In particular, in accordance with the prior art this is accomplished by way of the vial that contains the medical substance, such as a powder, being at negative pressure, so that after the connection to the other vial has been established, the liquid contained in the latter can be drawn in.

If filters are present, they should be embodied as planar filters. In this, the filter fabric is placed between two surface planes. For the purpose of achieving a uniform distribution of the liquid, the entire surface that contains filter fabric may be provided with regular centrally extending depressions. The supply and discharge of the liquid preferably takes place via four symmetrically arranged and centrally extending channels, which guide the liquid to central depressions. The protuberances in the surface serve as support of the fabric, i.e. as supporting surface.

The female Luer cone, such as a Luer-Lock cone, allows a problem-free withdrawal of the prepared medical agent, without any need for a metal cannula. Thus, a withdrawal without the need for a needle is possible.

The external screw threads, which are used to connect the two adapters, also provide an extreme rigidity. This allows an easier handling, in particular when attaching the vial. At the same time, it provides protection for the Luer connection against damage and leakage.

The modular design facilitates the combination of different vials of different sizes.

Moreover, it is also possible that from the adapter that accommodates the vial with the medical substance, such as lyophilisate, originate one or several projections, which prevent the device from rolling away in the event of careless handling. Instead of a projection, at least one the adapters may possess an exterior geometry that is different from that of a cylinder, e.g. a cuboid geometry.

For fastening the receptacle, it is in particular intended that the circumferential wall of the insert, which in particular is encompassed concentrically by the exterior circumferential wall of the outer body such as a housing, comprises projections, which extend radially into the interior of the insert, for holding the receptacle, whereby the circumferential wall at least in the area of the projections extends at some distance to the inside of the outer exterior circumferential wall.

The projections are in particular intended to engage behind a bead-like rim of the vial. In order for the elastically bendable projections, which originate from wall sections of the circumferential wall, to be adjustable to the required extent, the circumferential wall at least in the area of the projections extends spaced apart from the exterior circumferential wall. In particular it is intended that the circumferential wall extends spaced apart from the exterior circumferential wall everywhere.

In order to facilitate a simple aligning of the insert with respect to the adapter, a further development of the invention intends that the hollow-cylindrical sections, which for example are embodied as Luer cones, originate from the partition walls of the adapters. In contrast, the hollow-needle body, which preferably is embodied as a plastic spike and can also be referred to as a cannula body, extends from the bottom wall of the associated insert, extending in the opposite direction than the hollow-cylindrical section.

This however does not restrict the invention's scope. Of course it is also possible, for example, for the hollow-cylindrical section and the hollow-needle body to originate from the bottom wall or the partition wall.

To create a restrictor for the flowing liquid, the invention's mixing device may be further developed in such a way that at least in one of the adapters the bottom-sided or partition-wall-sided cross-section of the cannula body is smaller than the cross-section of the connecting opening extending on the bottom side or partition-wall side, which represents the connection to the hollow-cylindrical section, such as a Luer cone.

The restrictor should be provided in the respective adapter that accepts the vial containing the liquid.

The filter, which in particular is embodied as a two-dimensional filter element, extends between the bottom wall and the partition wall of the adapter, whereby in particular each adapter contains a corresponding filter element.

The exterior bottom surface of the insert, along which extends the filter, should be structured to prevent a planar contact of the filter element.

In this, the step in cross-section that creates a restriction between the hollow-cylindrical section such as Luer cone and the cannula body, such as a plastic spike, is only required in the respective adapter that is connected to the vial containing the liquid.

As a further development, the invention intends that the insert comprises a cylindrical first section that extends on the bottom side and a second section with a greater outside diameter that forms the circumferential wall diameter, and that on the outside the step is supported on a projection that axially protrudes from the partition wall of the hollow-cylindrical outer body.

Irrespective of this, it is in particular intended that the insert is joined circumferentially in a liquid-tight manner with the hollow-bodied outer body, whereby this in particular is embodied as a material bond, which may be created by ultrasonic welding.

With respect to the hollow-cylindrical sections that form the fluid connection, it is intended that from the partition wall of the hollow-cylindrical outer body, which possesses the internal tread, protrudes a male hollow-cylindrical section, such as a male Luer cone, which, when the adapters are being screwed together, engages in a liquid-tight or essentially liquid-tight manner in a female hollow-cylindrical section—protruding from the partition wall of the hollow-cylindrical outer body comprising the external thread—such as a female Luer cone or Luer Lock cone, or vice versa.

In order to achieve the desired flexibility of the insert for taking hold of a vial, it is possible that the circumferential wall of the insert has cut-outs at least in some areas between the bottom wall or the step and the radially inward pointing projection.

The hollow-cylindrical outer body and the insert present therein in particular are embodied as injection-molded parts.

Further details, advantages, and features of the invention are not only found in the claims, the characteristic features contained therein—individually and/or in combination—but also in the following description of a preferred embodiment example that is shown in the figures.

Figure 2:
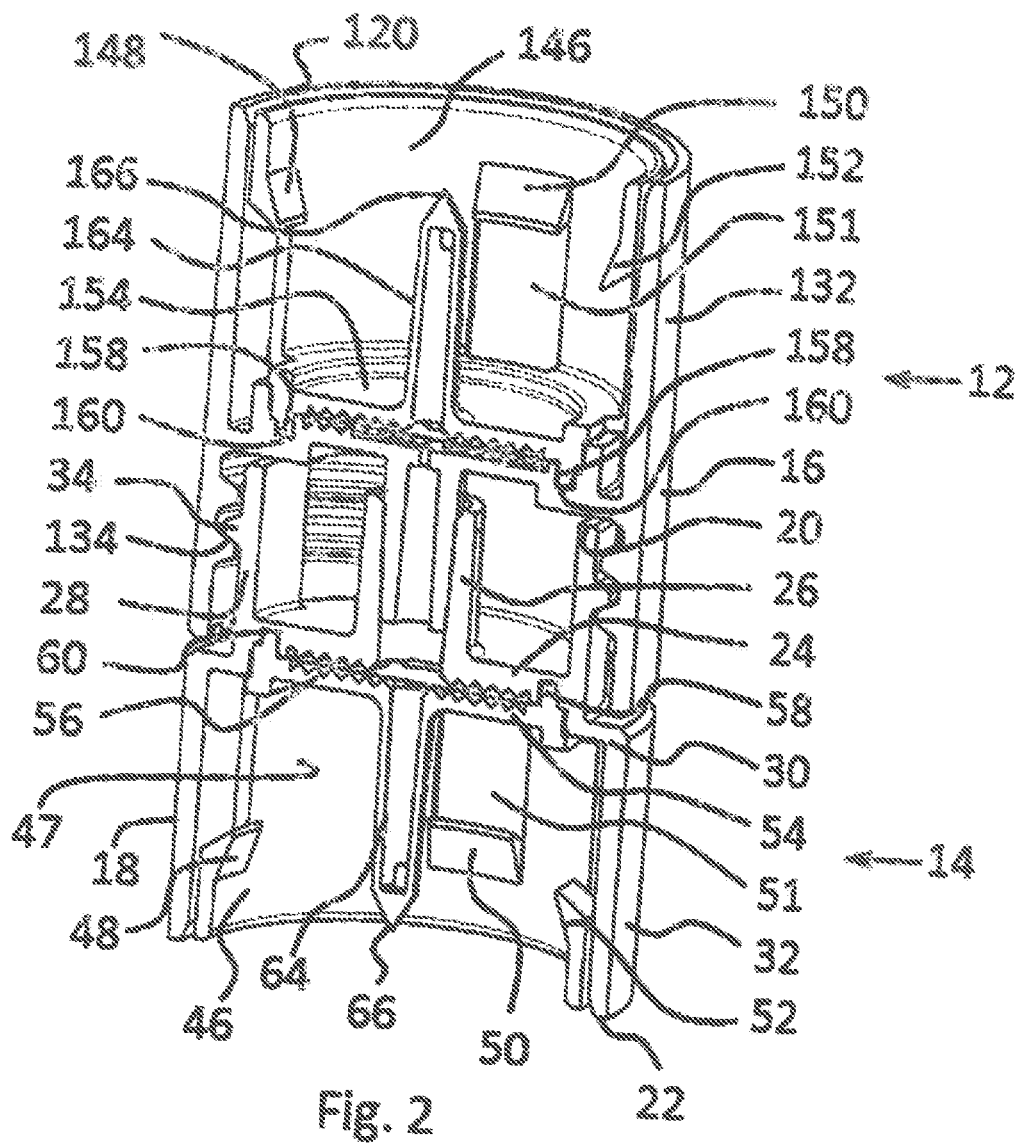
Figure 3:
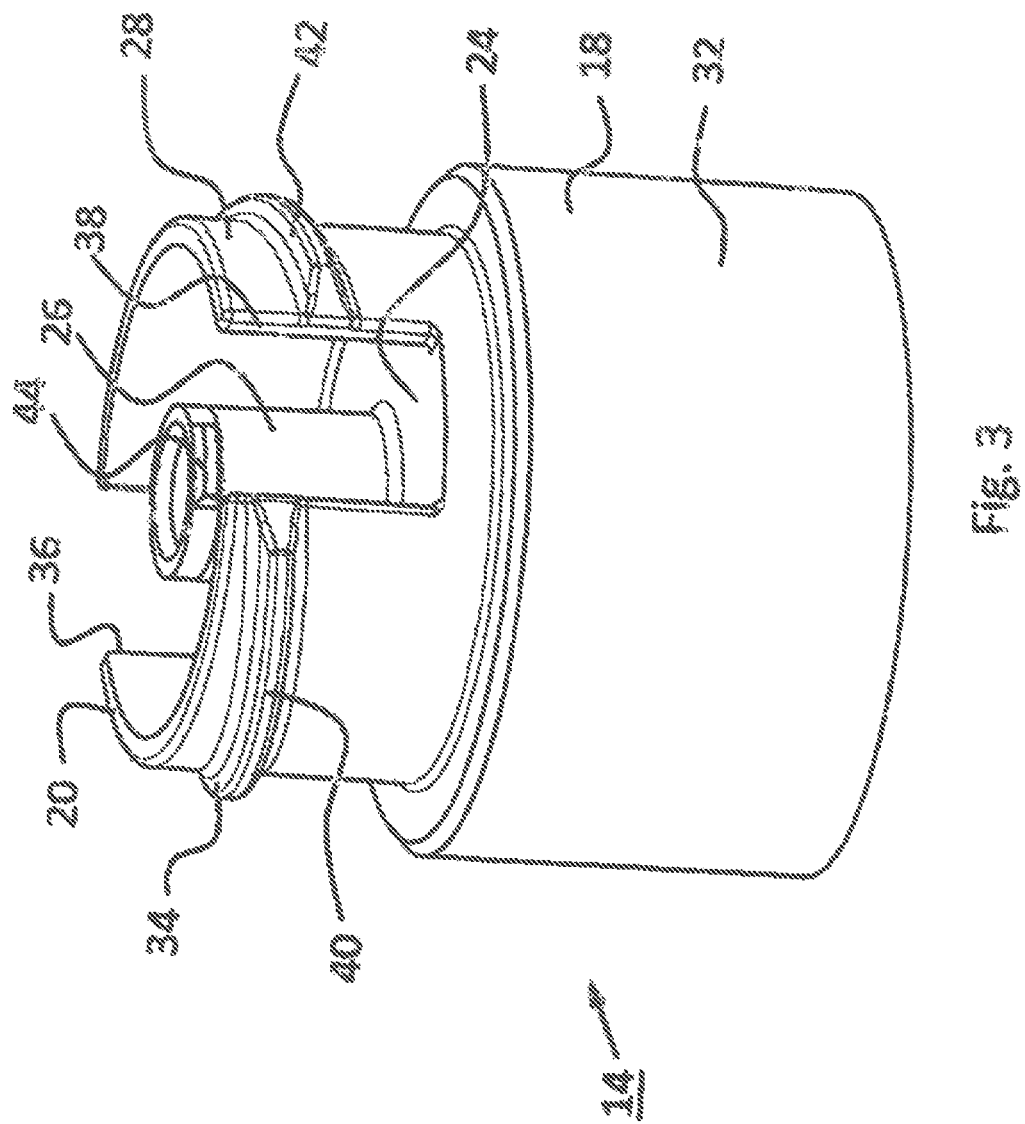
Figure 4:
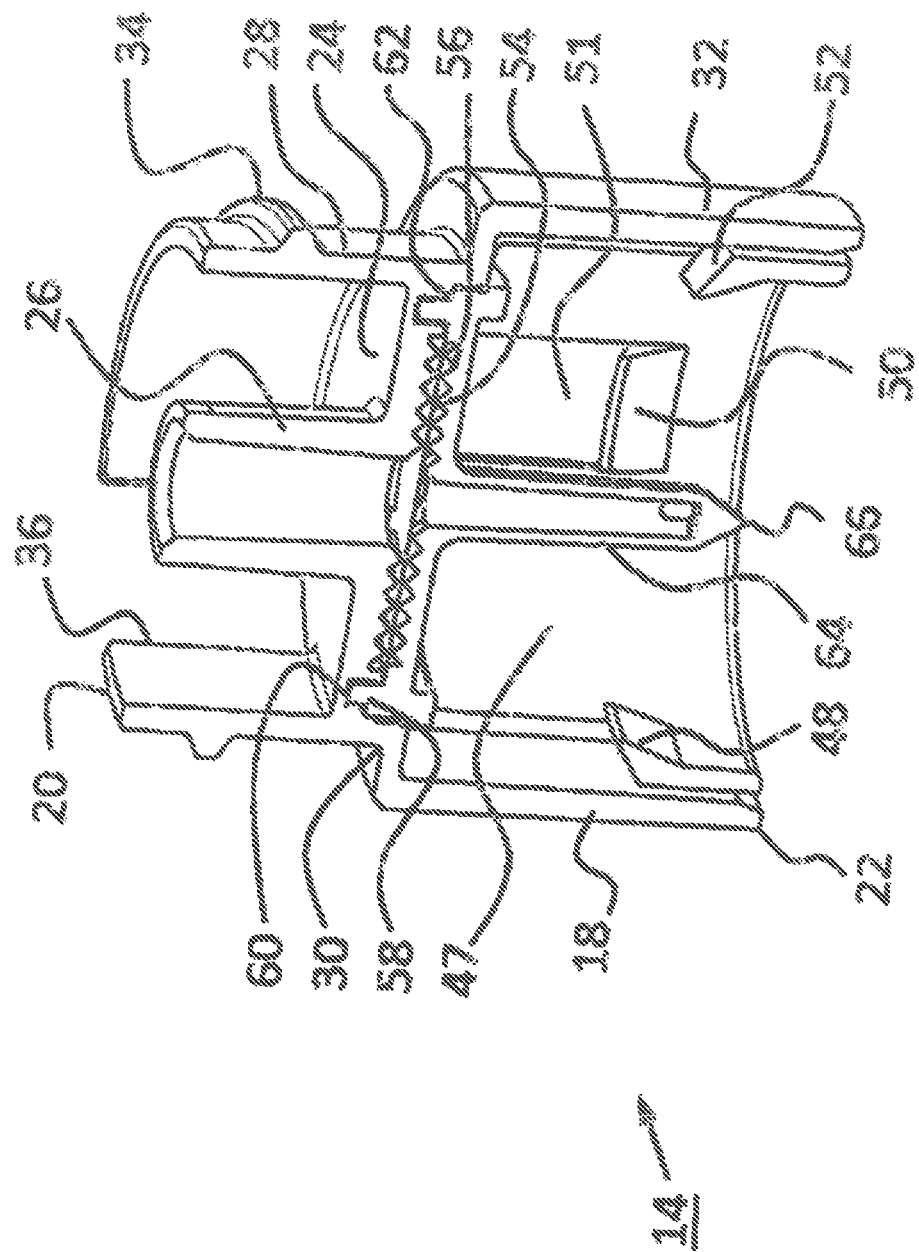
Figure 5:
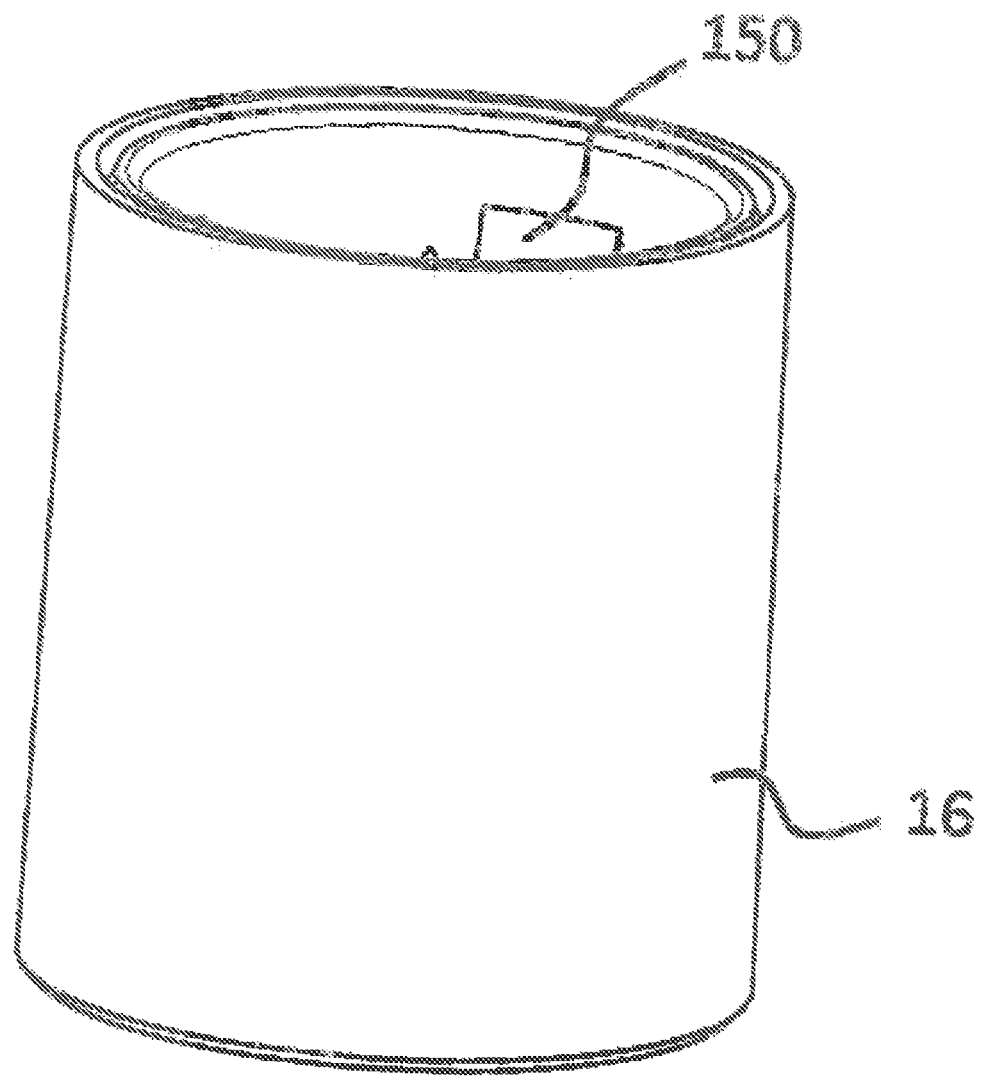
Figure 6:
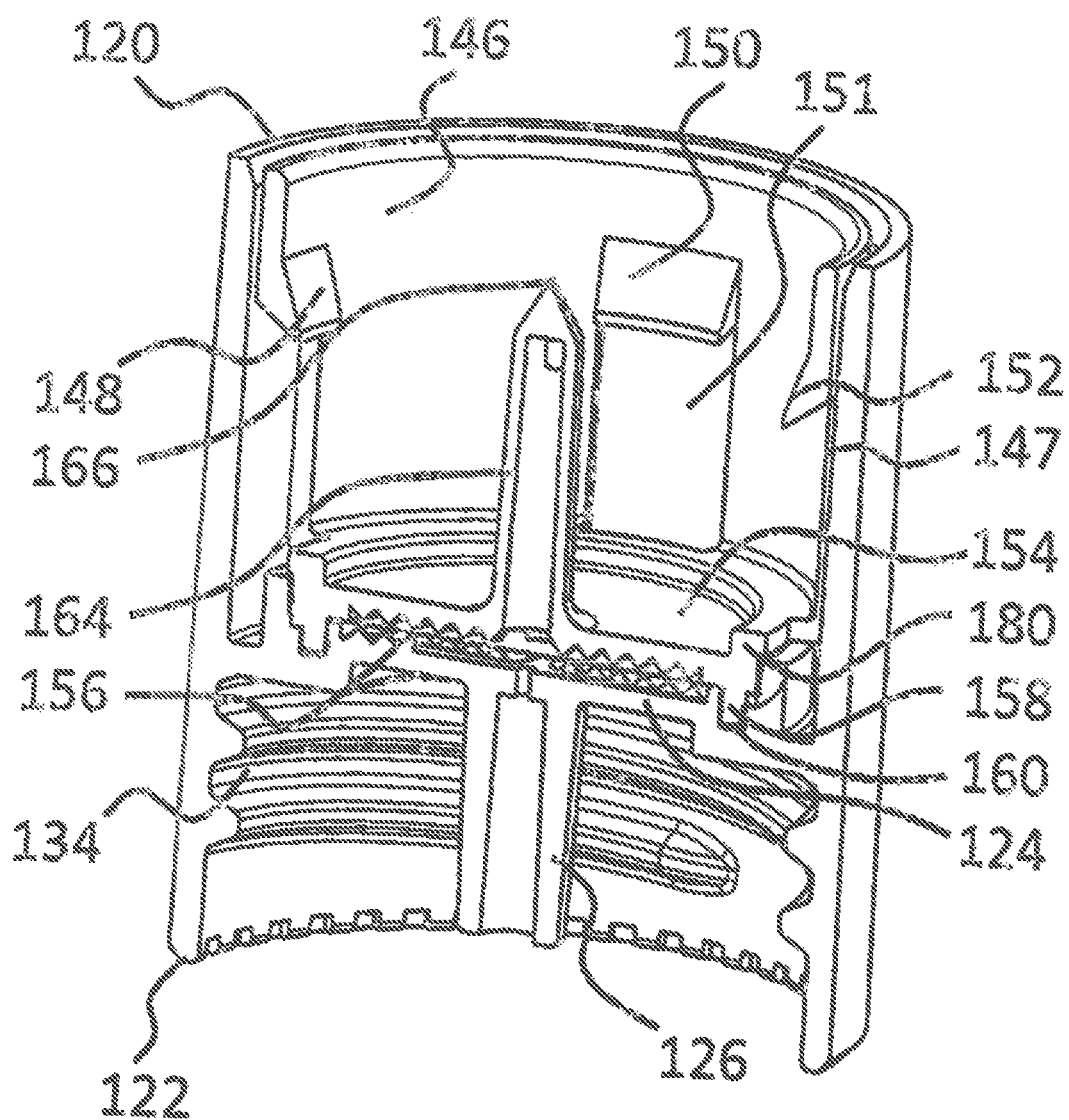
Figure 7:
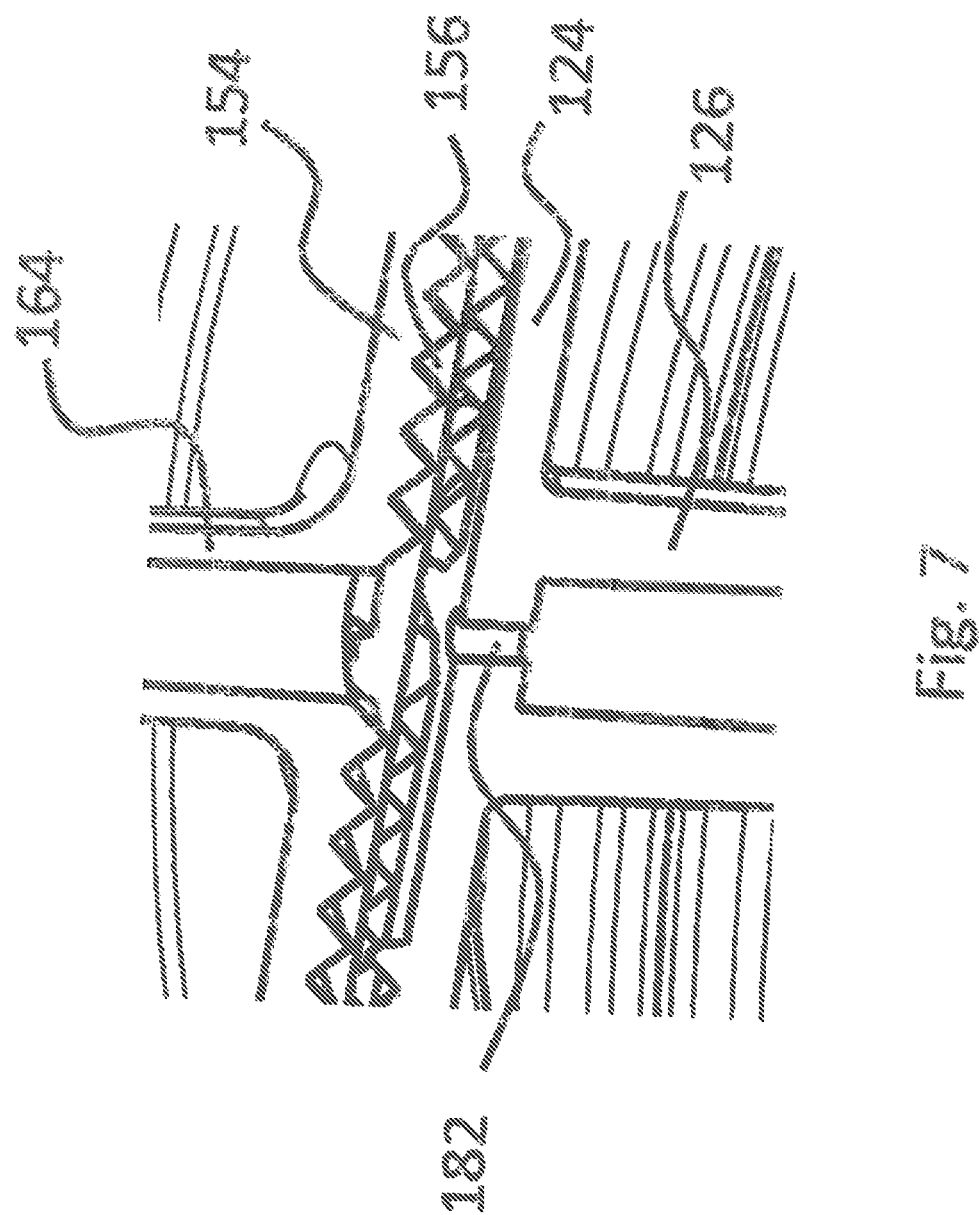
Figure 8:
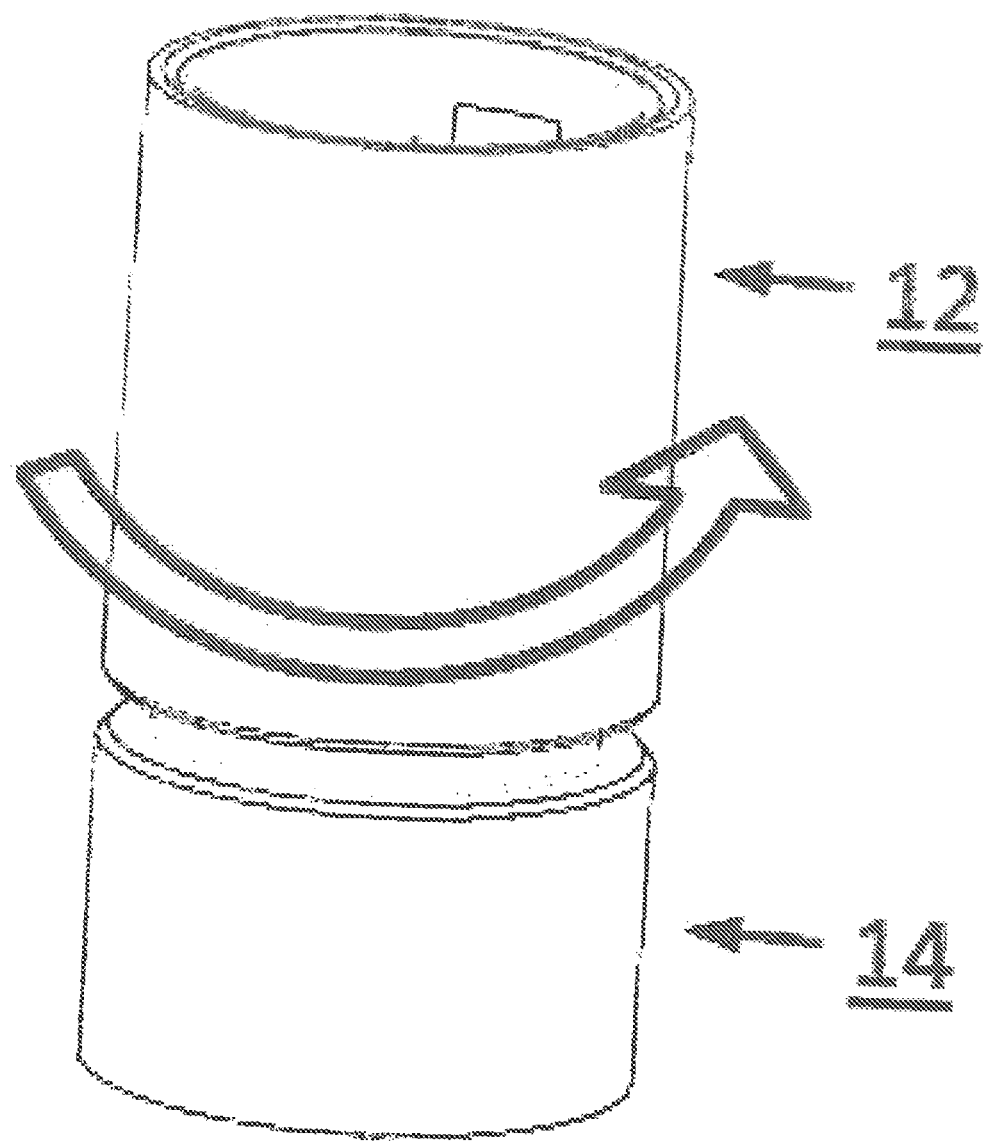
Figure 9:
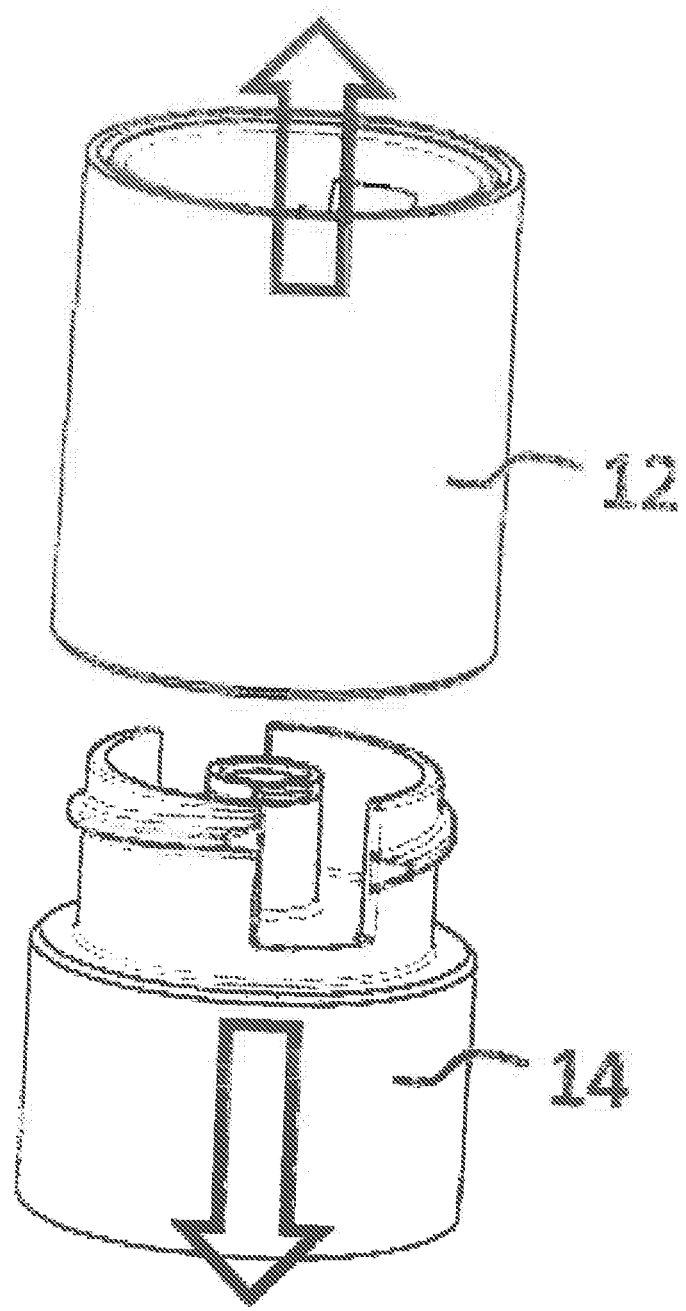
Figure 10:
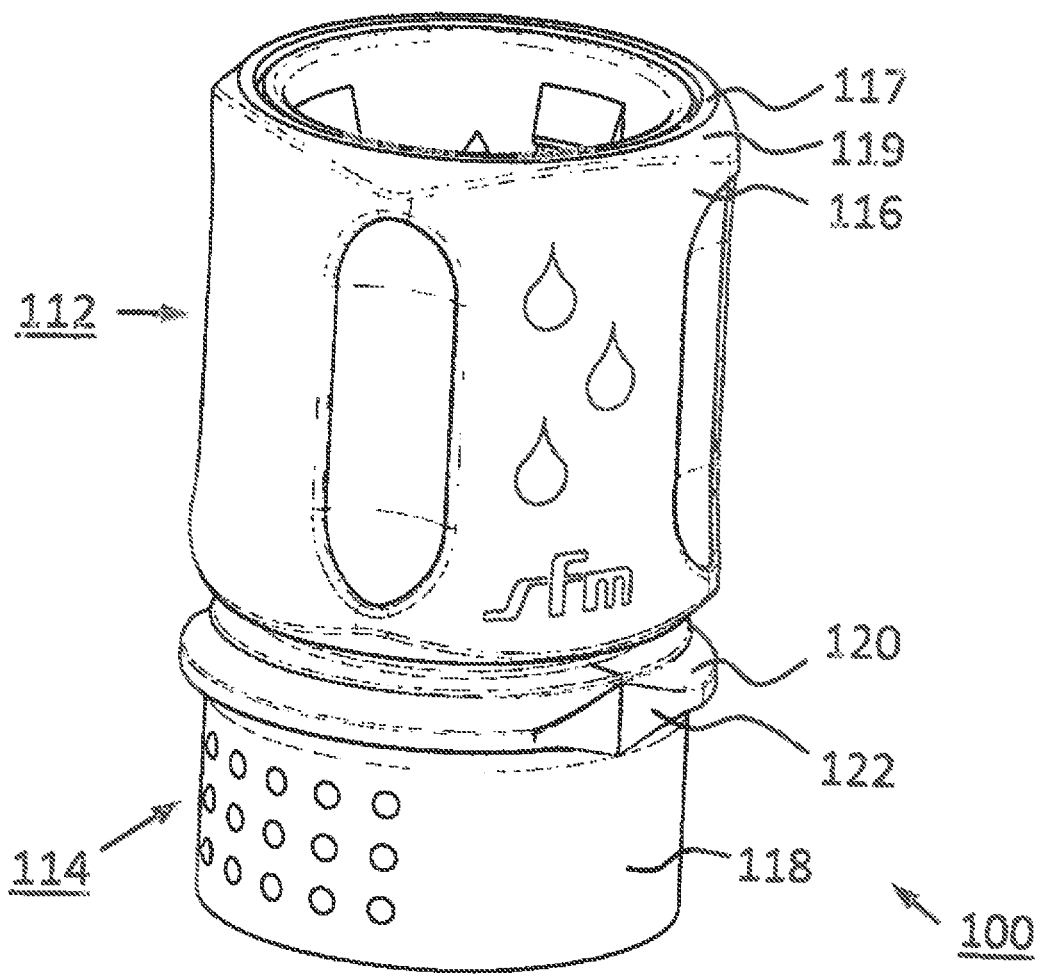

The figures show:

FIG. 1 shows a transfer-mixing device assembled from two adapters,

FIG. 2 shows a longitudinal sectional view of the transfer-mixing device of FIG. 1, FIG. 3 shows one of the adapters of the mixing and transfer device of FIGS. 1 and 2, FIG. 4 shows a sectional view of the adapter of FIG. 3, FIG. 5 shows the other adapter of the mixing and transfer device of FIGS. 1 and 2, FIG. 6 shows a sectional view of the adapter of FIG. 5, FIG. 7 shows a detail of the adapter of FIG. 6, FIG. 8 shows the second adapter in a position rotated relative to the first adapter, to facilitate separation, FIG. 9 shows the adapters after separation, and FIG. 10 shows a further embodiment of a transfer-mixing device.

The figures, in which identical elements always have the same reference label, show schematic drawings of a mixing and/or transfer device 10. For simplicity's sake, the mixing and/or transfer device 10 shall be referred to as mixing device 10 hereinafter.

Fundamental elements of the mixing device 10 are two adapters 12, 14, which are connected by means of a screwed connection. The adapters 12, 14 serve to accept receptacles or small bottles, which are not illustrated, are referred to as vials, and contain substances that are to be mixed together. For this purpose, it is in particular intended that one vial contains a medical substance, in particular in form of a lyophilisate while the other vial contains a liquid. The lyophilisate is under negative pressure so that when a link is established between the vials, the liquid from one of the vials is drawn into the vial containing the lyophilisate, so that a blending can occur to make the medication available for use.

The adapter 12 in the embodiment example serves to accept a vial that contains the liquid while the adapter 14 serves to accept the vial that contains the medical substance.

Each of the adapters 12, 14 comprises a respective hollow-cylindrical outer body 16, 18, which can be referred to as a housing, which in the embodiment of FIGS. 1 to 9 is closed along its circumference and in particular consists of a dimensionally stable plastic in order to guarantee dimensional stability, so that when the mixing device 10 is being handled it is in principle non-deformable. Hollow-cylinder- or hollow-cylindrical outer body or housing are to be seen as synonyms, whereby hereinafter for simplicity's sake the upper housing of the figure will be referred to as upper housing 16 and the housing of the adapter 14 will be referred to as lower housing 18.

In the embodiment example of FIGS. 1 to 9, the outer body, i.e. the housings 16, 18, possess a hollow-cylindrical geometry. In the embodiment example of FIG. 10, the housing 118 of the depicted lower adapter 114 also has a hollow-cylindrical geometry, whereas the upper outer body 116 of the upper adapter 112 externally has the cross-sectional geometry of a polygonal column, such as a square cross-sectional external geometry, but on the inside has a circular cross-sectional geometry. For reasons of simplification, the term hollow-cylindrical geometry will always be used, even if—as explained above—there may be deviations, which will be within the scope of the invention. To this extent, the term hollow-cylindrical outer body is to be understood as a synonym for all possible hollow-body geometries. Essential is that according to the invention's teaching the outer body can serve the function of accepting vials, in particular via an insert, as will be explained in the following.

From the lower housing 18 protrudes a, for example, triangular projection 15, which serves as an anti-rolling protection when the housing 18 is laid down. The shape of the projection 15 should be considered to be purely exemplary.

However, it is also possible to embody an anti-rolling protection in other ways, in particular by way of the polygonal column geometry of FIG. 10. In this respect we refer to the explanations in the following.

In the following we will at least explain the lower housing 18. The sectional view illustrates that between the front edges 20, 22 extends a partition wall 24 perpendicular to the longitudinal axis of the lower housing 18, and from the centre of which originates a hollow-cylindrical section, which for simplification's sake but in no way limiting the scope of protection is referred to as female Luer Lock cone 26 hereinafter, and which is coaxially surrounded by the upper wall section 28 of the lower housing 18, and which extends between the partition wall 24 and the upper, with respect to the figure, front edge 20.

The upper wall section 28 transitions via a step 30 into a lower wall section 32, which also possesses a cylindrical geometry.

In addition, from the outer surface of the upper wall section 28 originates an external thread 34 or rather sections of such and consequently a helically extending ledge, which by cut-throughs or cut-outs 36, 38 in the wall section 28 is subdivided into sections 40,42.

The cut-outs 36, 38 serve a function in particular during the manufacturing process, to allow a demolding of the housing 18, which is manufactured as an injection-molded part, since in this area extend ledge-like projections that radially protrude from the female Luer Lock cone 26. One of these projections is marked with the reference label 44.

According to the invention, an insert 46 is introduced into the region of the housing 18 that is surrounded by the lower wall section 18, i.e. the outer circumferential wall of the lower housing 18, and the partition wall 24, whereby the insert in particular is connected to the partition wall 24 in a material bond, preferably circumferentially. The insert 46 comprises a circumferential wall 47, which extends coaxial relative to the lower wall section 32, and which consequently extends concentrically around the longitudinal axis of the lower housing 18, and serves as accommodation or holder for the vial to be secured in position in the insert 46. For this purpose, projections 48, 50, 52 protrude from the circumferential wall 47 of the insert 46 and extend into the interior of the insert 46, whereby these projections possess a hook-shaped geometry, i.e. a triangular geometry in a sectional view, in order to, after proper insertion of a vial, engage behind the latter's collar-like rim and in this manner ensure that the position can be secured.

In order to guarantee a required flexibility of the projections 48, 50, 52, the insert 46, i.e. its circumferential wall 47, extends at least in the area of the projections 48, 50, 52, but preferably along the entire circumference, spaced-apart relative to the inner side of the outer circumferential wall 32 of the lower housing 18. Also provided are recesses, which extend between the projections 48, 50, 52 and the bottom wall 54, extending along the partition wall 24, of the insert 46. One of the recesses is marked with the reference label 51.

As already mentioned, when the insert 46 is fixed in position, the bottom wall 54 extends along the outside of the partition wall 24 of the lower housing 18, whereby between the outer side of the bottom wall 54 and the outer side of the partition wall 25 a planar filter 56 is provided. The filter may be secured in advance in a position at the outside of the bottom wall 54 of the insert, before the insert 46 is inserted into the lower housing part 32 and connected with the latter.

To guarantee a proper positioning of the insert 46, the bottom wall 54 comprises a ledge 58, which is circular and circumferentially protrudes beyond the insert's outer side, whereby the ledge can be inserted into a corresponding recess 60 in the outer side of the partition wall 24, in order to facilitate a centering in this manner. Other centering measures are also possible and are within the invention's scope. Centering means of this type also include centering means in individual points.

Furthermore, in the area of the interior side of the step 30 of the lower housing 18 the insert 46 may comprise a step 62, which further guarantees the desired coaxial alignment of the insert 46 relative to the lower housing 18.

In the area of the ledge-like projection 58, the insert 46 should be joined to the partition wall 24, in particular firmly bonded by means of ultrasonic welding, for example, which ensures a liquid-tightness between the insert 46 and the partition wall 24.

From the bottom wall 54 extends, extending oppositely relative to the female Luer Lock cone 26, a plastic spike 64, which forms a hollow-needle body or cannula body, with a tip 66, which upon insertion of the vial into the insert 46 pierces the vial's closure, so that in the manner described in the following a connection is established via the female Luer Lock cone 26 to the vial accommodated in the upper housing 16 of the mixing device 12.

As is particularly evident in the sectional view, the cross section, i.e. the lumen, of the spike 64 in the passage opening through the bottom wall 54 and the partition wall 24 possesses a smaller cross-section than the Luer Lock cone 26 extending on the partition-wall side, i.e. bottom-wall side.

Equivalent to the explanation in connection with FIGS. 3 and 4, an insert 146 may be introduced into the upper housing 16, which is surrounded coaxially by the outer wall 132 of the upper housing 16 and in particular extends along the circumference side entirely spaced-apart relative to the inside of said outer wall. The insert 146 also comprises a bottom wall 154, from which protrudes a plastic spike 164, which includes a tip 166, serves in the function of a cannula body, and extends along the longitudinal axis of the mixing device 10 and consequently of the upper housing 16. Consequently, the spike 164 is coaxially surrounded by the circumferential wall 147 of the insert 146.

Present in the circumferential wall 147 are recesses 151, which are bordered by hook-shaped projections 148, 150, 152, which protrude radially into the interior of the insert 146, and which, as per the explanations provided above, serve to engage behind the rim of a vial to be accommodated by the insert 146. In this respect we refer to the explanations provided above.

FIG. 4 illustrates that from the bottom wall 154 of the insert 146 originates a ledge-like projection 158, which extends axially and extends along a circle, and which engages in a associated recess, such as a groove 160, in the partition wall 124 that extends between the front edges 122, 120 of the upper housing 16.

From the partition wall 124 originates a hollow-cylindrical section 126, such as a Luer cone, which extends along the longitudinal axis of the upper housing 16 and which, when the adapters 12, 14, i.e. the housings 16, 18, have been assembled, engages in the female Luer Lock cone 26. For reasons of simplicity, the hollow-cylindrical section 126 is referred to as Luer cone hereinafter, without this limiting the invention in any way.

Along the exterior surface of the bottom wall 154 of the insert 146 extends a filter 156, which is connected to the exterior surface before the insert 146 is joined in a material bond, e.g. by welding, to the partition wall 124. However, it is also possible to embody the adapter 12 without a filter 156. On the other hand, the adapter 14 should comprise a filter 56.

Deviating from the embodiment of the insert 46 of the lower housing 18, the bottom wall 154 of the insert 146 joins with the circumferential wall 147 via a step 180, so that the insert 146 basically is composed of two cylindrical sections, namely the one bordered by the bottom wall 154 and the outer hollow-cylindrical section of larger cross-section, from which the projections 146, 150 protrude radially inward.

Furthermore, between the partition wall 124 and the front wall 122 that faces the lower housing 18 extends a groove-like depression that forms an internal thread 134, which in the embodiment example consists of two convolutions as is shown in the sectional view of FIG. 2. However, the invention is not restricted by the number of convolutions. In fact, the internal external thread 34 of the lower housing 18 engages into the internal thread 134 when the housings 16, 18, i.e. the adapters 12, 14 are to be connected.

The detailed illustration of FIG. 7 shows particularly well that the filter 156 extends between the partition wall 124 of the upper housing 16 and the bottom wall 154 of the insert 146.

In particular, it is also evident in the detailed illustration that the bottom-side cross-section of the spike 164, which originates at the partition wall 124 and forms a hollow-needle body or cannula body, is greater than the passage opening 182 of the Luer cone 126 through the partition wall 124, which causes the formation of an aperture between the spike 164 and the Luer cone 126, which serves to restrict the liquid flowing through the spike 164, the Luer cone 126, and via the spike 64 into the vial, which was pierced by the spike, and contains the lyophilisate.

In accordance with FIGS. 8 and 9, the inside and outside threads 34, 134 are embodied in such a way that after a relative rotation of approximately 180° between the upper and lower adapters 12, 14, detaching the two becomes possible or a connection between the two has been secured, whereby the Luer cone 126 penetrates into the female Luer Lock cone 26 in such a way that an adequate relative sealing is achieved and consequently the liquid can flow from one vial into the other vial.

Irrespective hereof, the figures are self-explanatory and render the features that characterize the invention to an adequate degree.

As already mentioned, the transfer device 100 of FIG. 10 differs from the one of FIGS. 1 to 9 solely by its outer shape and not by the accommodations for the vials, which according to the present invention are embodied as inserts. The upper housing 116 may be manufactured using a two-component plastic injection-moulding process. In this, the upper housing 116 consists of an inner base body 117, which possesses a hollow-cylindrical geometry and along its circumferential side has been partially over-molded with a thermoplastic elastomer (exterior layer 119). These regions are responsible for the over-molded upper housing 116 possessing the external geometry of a polygonal column. This results in better haptics, since the transfer device 100 fits better into the hand and becomes easier to handle and also softer. Since the media to be mixed are refrigerated when stored, and the transfer device 114 is supplied in the same package as these media, one reaps the benefit that because of the thermoplastic coating (exterior layer 119) the upper housing 116 seems 'warmer' to the touch.

The recesses shown in FIG. 10 are clearances in the exterior layer 119, through which the base body 117 can be handled.

FIG. 10 further illustrate that the lower housing 118 possesses in its upper edge region a circumferentially protruding rim 120, which is intended to facilitate the handling of the lower housing 118 when it is being screwed together with the upper housing 116. For this, the rim 120 additionally possesses diametrically opposed flat areas 122 or rather V-shaped depression in a sectional view. One of these is illustrated in FIG. 10.

The lower housing 118 in particular consists of an acrylic polymer. The upper housing 116 as well as the inserts 46, 146 may consist of methyl methacrylate, acrylonitrile, butadiene, and styrene (MABS).

The transfer device itself can have a height of for example 46 mm and a diameter of 30 mm. The wall thickness of the lower housing 18, 118 and the upper housing 16 or base body 117 should be in the region between 1.2 mm and 1.6 mm.

The invention claimed is:

1. A device for mixing or transferring a first substance and a second substance that are present, respectively, in a first and a second receptacle, comprising:
    a first adapter having a circumferential wall, and being configured to accept the first receptacle, and along which extends, and which, at least in sections, surrounds a first cannula body, and a first hollow-cylindrical section connected to the first cannula body,
    a second adapter having a circumferential wall, and being configured to accept the second receptacle, and along which extends, and which, at least in sections, coaxially surrounds, a second cannula body, and a second hollow-cylindrical section connected to the second cannula body,
    wherein, in an assembled state, the first hollow-cylindrical section inter-engages with the second hollow-cylindrical section, and the first adapter and the second adapter are screwably and detachedly connected,
    wherein each of the first and the second adapters comprises a hollow-cylindrical outer body with an exterior circumferential wall, and a partition wall extending perpendicularly to a longitudinal axis of the outer body,
    wherein, when the first and second adapters are assembled together, a section, which has an inner thread, of the outer circumferential wall of one of the first and the second adapters surrounds a section, which has an external thread, of the outer circumferential wall of the other of the first and the second adapters, with inter-engaging threaded sections,
    wherein the hollow-cylindrical outer body of at least one of the first and second adapters comprises an insert, having a circumferential wall, that accepts the first or the second receptacle, and
    wherein the circumferential wall of the insert extends, at least in sections of the interior surface of the outer circumferential wall, spaced-apart from the interior surface of the outer circumferential wall.

2. The device according to claim 1, wherein each of the first and second adapters comprises an insert with a circumferential wall that accepts the first or the second receptacle.

3. The device of claim 1, wherein the circumferential wall of the insert, which is concentrically surrounded by the outer circumferential wall of the outer body comprises projections that radially extend into the interior of the insert for holding the receptacle, whereby the circumferential wall at least in the area of the projections extends spaced-apart relative to the interior side of the outer circumferential wall.

4. The device of claim 1, wherein the insert comprises a bottom wall, which, when the insert is connected with the hollow-cylindrical outer body, is supported on the partition wall.

5. The device of claim 4, wherein the circumferential wall of the insert is recessed in at least some areas between the bottom wall, or the step, and the radially inward protruding projection.

6. The device of claim 4, wherein the bottom wall of the insert is supported on the partition wall via a filter element.

7. The device of claim 1, wherein, from the bottom wall of the insert protrudes, extending in the opposite direction than the circumferential wall, a centering element, which, when the hollow-cylindrical outer body is connected to the insert, engages into an adapted acceptance in the partition wall or vice versa.

8. The device of claim 7, wherein the centering element is configured as an annularly extending ledge element, which engages into an annularly extending recess.

9. The device of claim 1, wherein, from the bottom wall of the insert originates the cannula body and/or from the partition wall of the hollow-cylindrical outer body originates the hollow-cylindrical section.

10. The device of claim 1, wherein, in at least one of the first and second adapters, the effective cross section of the cannula body in the bottom wall is greater than the cross-section of a connecting opening leading to the hollow-cylindrical section that originates from the partition wall.

11. The device of claim 1, wherein, when the first and second adapters have been screwed together, external surfaces of the first and second adapters form a substantially flush transitional surface.

12. The device of claim 11, wherein the external surfaces of the first and second adapters are solid.

13. The device of claim 11, wherein a gap extends between the external surfaces of the first and second adapters.

14. The device of claim 1, wherein an exterior side of the bottom wall of the insert is structured.

15. The device of claim 14, wherein the bottom wall is covered by a planar filter element.

16. The device of claim 1, wherein the insert comprises a hollow-cylindrical first section extending on the bottom side and, via a step as transition, a second section of greater external diameter that forms the circumferential wall, and in that the step is supported on a projection that axially protrudes from the partition wall of the hollow-cylindrical outer body.

17. The device of claim 1, wherein the insert is circumferentially connected to the hollow-cylindrical outer body in an airtight or liquid-tight manner.

18. The device of claim 1, wherein on the bottom side, the insert is connected in a materially bonded manner to the hollow-cylindrical outer body, in particular by means of ultrasonic welding.

19. The device of claim 1 wherein from the partition wall of the hollow-cylindrical outer body that possesses the internal thread protrudes a male hollow-cylindrical section which engages liquid-tight or essentially liquid-tight with a female hollow-cylindrical section which protrudes from the partition wall of the external-thread-equipped outer body, when the first and second adapters have been screwed together, or vice versa.

20. The device of claim 19, wherein the male hollow-cylindrical section is configured as a male Luer lock cone, and the female hollow-cylindrical section is configured as a female Luer lock cone.

21. The device of claim 1 wherein the hollow-cylindrical outer body and/or the insert are/is embodied as an injection-molded part.

22. The device of claim 1 wherein at least one of the hollow-cylindrical outer bodies possesses on the inside a cylindrical geometry and on the outside a geometry different from a cylindrical geometry.

23. The device of claim 22, wherein the geometry that is different from a cylindrical geometry is a polygonal-column geometry.

24. The device of claim 1, wherein at least one of the hollow-cylindrical outer bodies is manufactured in a two-component injection-molding process.

25. The device of claim 1, wherein the at least one hollow-cylindrical outer body comprises an inner base body, which possesses a hollow-cylindrical geometry and which is partially over-molded.

26. The device of claim 25, wherein the hollow-cylindrical geometry is partially over-molded to create a polygonal-column external geometry.

27. The device of claim 1, wherein the first hollow-cylindrical section engages with the second hollow-cylindrical section in a liquid-tight manner.

28. The device of claim 1, wherein the circumferential wall of the insert extends entirely around the interior surface of the outer circumferential wall.

* * * * *